(12) United States Patent
Stuermer et al.

(10) Patent No.: US 10,092,746 B2
(45) Date of Patent: Oct. 9, 2018

(54) IMPLANTABLE DEVICE

(71) Applicant: BIOTRONIK SE & Co. KG, Berlin (DE)

(72) Inventors: Uwe Stuermer, Berlin (DE); Thomas Doerr, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 0 days.

(21) Appl. No.: 14/609,607

(22) Filed: Jan. 30, 2015

(65) Prior Publication Data

US 2015/0251005 A1    Sep. 10, 2015

Related U.S. Application Data

(60) Provisional application No. 61/948,576, filed on Mar. 6, 2014.

(51) Int. Cl.
*A61N 1/08* (2006.01)
*A61N 1/05* (2006.01)
*G01R 31/02* (2006.01)

(52) U.S. Cl.
CPC .............. *A61N 1/08* (2013.01); *A61N 1/056* (2013.01); *G01R 31/021* (2013.01)

(58) Field of Classification Search
CPC .......... A61N 1/08; A61N 1/056; G01R 27/04; G01R 27/06; G01R 31/021; H04B 1/0466; A61B 2018/00785
See application file for complete search history.

(56) References Cited

U.S. PATENT DOCUMENTS

| RE31,728 E | * | 11/1984 | Simmonds | G01R 31/021 379/21 |
| 5,212,453 A | * | 5/1993 | Koehler | G01R 27/06 324/533 |
| 5,649,969 A | * | 7/1997 | Abrahamson | A61N 1/05 600/510 |

(Continued)

OTHER PUBLICATIONS

European Search Report and Notes to the European Search Report on European Patent Application No. EP 15 15 4830, dated May 8, 2015 (6 pages).

*Primary Examiner* — Son Le
*Assistant Examiner* — Dustin Dickinson
(74) *Attorney, Agent, or Firm* — Buchanan Ingersoll & Rooney PC

(57) ABSTRACT

A test apparatus for an implantable electrode line and also for an electrode line and an implantable device, including a directional coupler or a circulator for coupling an electrical test symbol into at least one electrical conductor of the electrode line and for decoupling the reflected test signal from the electrical conductor of the electrode line. Such a directional coupler makes it possible to couple a test signal, e.g., a steep voltage pulse, into an electrical conductor of the electrode line and to decouple again the returning reflected voltage pulse (namely, the reflected test signal) from the electrical conductor by means of the directional coupler or circulator.

A method for testing an electrical conductor of an implantable electrode line including: 1) coupling a test signal into the electrical conductor; 2) decoupling the test signal reflected in the electrical conductor from the electrical conductor; and 3) evaluating the reflected test signal.

15 Claims, 3 Drawing Sheets

(56) References Cited

U.S. PATENT DOCUMENTS

| | | | |
|---|---|---|---|
| 6,101,415 A * | 8/2000 | Er | A61N 1/372 600/510 |
| 6,212,431 B1 | 4/2001 | Hahn et al. | |
| 2004/0183521 A1* | 9/2004 | Macphail | G01R 27/06 324/117 R |
| 2005/0264306 A1* | 12/2005 | Jung | G01R 31/2853 324/717 |
| 2006/0012376 A1* | 1/2006 | Furse | G01R 31/11 324/534 |
| 2010/0082025 A1* | 4/2010 | Brannan | A61B 18/18 606/33 |
| 2011/0077633 A1* | 3/2011 | Bonn | A61B 18/1815 606/33 |
| 2012/0197331 A1* | 8/2012 | Germanson | A61N 1/3706 607/11 |
| 2012/0290028 A1* | 11/2012 | Doerr | A61N 1/37241 607/6 |
| 2014/0018873 A1* | 1/2014 | Gunderson | A61N 1/3702 607/17 |
| 2014/0058481 A1 | 2/2014 | Perryman et al. | |
| 2014/0320154 A1* | 10/2014 | Arunachalam | G01L 27/007 324/750.3 |
| 2015/0222511 A1* | 8/2015 | Fertner | H04B 3/493 370/252 |

\* cited by examiner

IMPLANTABLE DEVICE

CROSS-REFERENCE TO RELATED APPLICATIONS

This patent application claims the benefit of U.S. Provisional Patent Application No. 61/948,576, filed on Mar. 6, 2014, which is hereby incorporated by reference in its entirety.

TECHNICAL FIELD

The present invention relates to an implantable device that is connected to, or is to be connected to, an electrode line. In particular, the present invention relates to implantable monitoring and/or therapy devices, such as neurostimulators, cardiac pacemakers, cardioverters, defibrillators and the like.

BACKGROUND

At least one stimulation electrode line that is typically connected to implantable cardiac pacemakers or defibrillators, and, at its proximal end intended for connection to the cardiac pacemaker or defibrillator, has a standardized electrical terminal, and, at its distal end intended for placement in the heart, has one or more electrode poles. Such an electrode pole is used to deliver electrical pulses to the tissue (myocardium) of the heart or to sense electrical fields in order to sense cardiac activity within the scope of what is known as sensing. For this purpose, electrode poles typically form electrically conductive surface portions of an electrode line. Electrode poles are typically provided as ring electrodes in the form of a ring around the electrode line, or in the form of a point electrode or tip electrode at the distal end of the electrode line. The electrode poles are electrically conductively connected via one or more electrical conductors to contacts of the electrical terminal of the electrode line at the proximal end thereof. One or more electrical conductors, which electrically connect one or more of the electrode poles to one or more of the contacts, thus run between the contacts of the electrical terminal of the electrode lines at the proximal end thereof and the electrode poles at the distal end of the electrode line. These electrical conductors can be used on the one hand for transmission of stimulation pulses to the electrode poles and, on the other hand, for transmission of electrical signals, received by means of the electrode poles, to the proximal end of the electrode line.

If an electrical conductor of the electrode line has a fault, this may mean that the transmission of stimulation pulses to the electrode poles or, in particular, also the transmission of electrical signals from the electrode poles to the proximal end of the electrode line is no longer reliable. In the case of an implantable device in the form of a cardiac pacemaker, this may lead to problems not only in the event of stimulation, but also in the event of sensing, with the result that intracardial events, for example, are not detected or are detected incorrectly. Faults of this type may occur for the first time during the course of operation of the electrode line, that is to say when the electrode line may already have been implanted for a relatively long period of time in a patient. Some implantable devices therefore contain a test apparatus, by means of which faults on the electrode line can be detected, where possible.

Known approaches for electrode fault detection utilize, for example, the measurement and evaluation of the following parameters:

electrode impedances
signal amplitudes
interference signal detection
stimulus thresholds
various plausibility tests The known methods for electrode fault detection continually demonstrate low sensitivity and specificity, however. For example, insulation defects on the electrode line thus may not be established at all by means of an impedance measurement, since the impedance of the actual electrode poles is much lower than a reduction of the impedance as a result of an insulation defect, such that the insulation defect leads only in the impedance test to an insignificant drop of the measured impedance. The same is true for the other mentioned methods.

The present invention is directed toward overcoming one or more of the above-mentioned problems.

SUMMARY

An object of the present invention is therefore to create a test apparatus which has maximum sensitivity and specificity in respect of electrode fault detection.

At least this object is achieved in accordance with the present invention by a test apparatus for an implantable electrode line, said apparatus comprising a directional coupler or a circulator for coupling an electrical test signal into at least one electrical conductor of the electrode line, and for decoupling the reflected test signal from the electrical conductor of the electrode line. A directional coupler of this type makes it possible to couple a test signal, for example, a steep voltage pulse, into an electrical conductor of the electrode line, and to decouple again the returning reflected voltage pulse (that is to say the reflected test signal) from the electrical conductor by means of the directional coupler or circulator. The test apparatus according to the present invention uses the effect that inhomogeneities, for example, of the impedance along an electrical conductor, cause an electric wave, for example, as accompanies a high-frequency test signal, to be reflected in part at locations of inhomogeneity of this type. Thus, whereas part of the wave fed in the form of the test signal into the electrical conductor is delivered from the electrode line into the surrounding environment, another part of this wave is partly reflected at various locations of the electrode line. A characteristic reflected test signal is thus produced. This characteristic reflected test signal is different for an intact electrode line than for a defective electrode line which, for example, has a break of an electrical conductor. In the latter case, the test signal would be reflected at the location of the break of the electrical conductor because the impedance increases there. Accordingly, a larger part of the test signal is reflected earlier in the case of a defective electrode line of this type than with an intact electrode line. As a result, a different reflected test signal is provided than with an intact electrode line. An electrode fault can therefore be identified on the basis of a test signal fed into a conductor of the electrode line by means of the directional coupler or circulator, partly reflected in the conductor of the electrode line and fed out again from the conductor of the electrode line via the directional coupler or circulator.

The test apparatus preferably comprises a test signal generator, which is connected to the directional coupler or the circulator and is designed to generate and to deliver a test signal to be coupled into the electrical conductor of the electrode line via the directional coupler or the circulator. Here, the test signal generator is preferably designed to generate a test signal having high-frequency signal components, for example, a steep voltage pulse.

In addition, the test apparatus preferably comprises an evaluation unit, which is connected at least indirectly to the directional coupler or the circulator and which is designed to evaluate a reflected test signal decoupled from the electrical conductor of the electrode line by means of the directional coupler or the circulator and to generate and to output a signal indicating a fault of the electrode line in accordance with a result of the evaluation. Here, the evaluation unit is preferably designed to compare a reflected and decoupled test signal with a reference signal, which has been recorded with a demonstrably intact electrode line. In particular, the evaluation unit is preferably designed to determine such properties of the decoupled reflected test signal, such as, for example, signal maxima and the duration between the delivery of a test signal and detection of a signal maximum of the reflected test signal, and to compare these with reference values. The evaluation unit may also be designed to carry out a morphology comparison between a reference signal for a reflected test signal and a respective test signal. In particular, a morphology comparison of this type may also include the determination of the period of time between delivery of a test signal and the detection of specific features of the reflected test signal.

A test apparatus is thus produced for improved detection of electrode faults, such as, for example, insulation defects, short circuits or line breaks on implanted electrode lines, in that, in accordance with the present invention, the HF reflection properties of the electrode line are assessed by the use of a directional coupler in the implant.

This test apparatus provides the advantage that defects on an electrode line can be detected in good time and reliably.

The directional coupler or circulator is preferably connected to the electrical conductor of the electrode line via a single-pole, double-throw switch (SPDT) suitable for high frequencies. It is thus possible to fully uncouple the electrical conductor from the typical component parts of an implantable device, such as, the component parts of a filter feedthrough, and to couple the electrical conductor exclusively to the test signal generator and the evaluation unit. A testing of the electrical conductor is then uncompromised by the other components of an implantable device. Conversely, the test apparatus can thus be prevented from compromising the regular operation of the implantable device with the electrode line. A double-throw switch of this type can be implemented, for example, as an MEMS relay or with the aid of transistors. MEMS relays have advantages in terms of electromagnetic interference (EMI) and are therefore preferred.

The directional coupler is preferably formed on the basis of microstrip technology. The directional coupler can thus be particularly small and can be integrated easily into an electrode line or a terminal housing (header) of an implantable device.

The directional coupler preferably has a bandwidth which comprises at least part of the frequency range between 400 MHz and 2.4 GHz, in particular, the frequency range between 400 MHz and 800 MHz. In the latter frequency range, the associated wave has a wavelength between approximately 40 to 70 cm, such that the wavelength or a half or a quarter thereof corresponds approximately to the length of the electrical conductor of the respective electrode line.

The test apparatus is preferably part of an implantable device that is connected or is to be connected to an electrode line. At least the aforementioned object is accordingly also achieved in accordance with the present invention by an implantable device that is connected or is to be connected to an electrode line and that comprises a test apparatus of the type described and claimed here. The test apparatus specifically not only has the advantage of having high sensitivity and specificity in the case of electrode fault detection, but can additionally also be formed so small that it can be integrated into an implantable device, such as, for example, a cardiac pacemaker/defibrillator or the like, or even into an electrode line.

The directional coupler or the circulator is preferably connected via a single-pole, double-throw switch, suitable for high frequencies, to the electrode line or to a terminal for an electrode line. The latter variant is advantageous with implantable devices that comprise a terminal having contact sockets (for example, electrical contact sockets) for an electrode line. In this case, the test apparatus or at least the directional coupler or the circulator can be connected in a switchable manner to the terminal for the electrode line. For normal operation, the terminal of the electrode line is connected by means of the double-throw switch to the electrical and electronic components of the implantable device provided for normal operation. The aforementioned advantages are thus provided, specifically in particular the possibility to use a filter feedthrough, even in the implantable device, without this filter feedthrough compromising the electrode fault detection, since it is only effective during normal operation of the implantable device.

In the case of an implantable device that has a terminal housing (also known as a header), in which the terminal for an electrode line is located, it is advantageous if at least the directional coupler or the circulator and, where applicable, also the single-pole, double-throw switch suitable for high frequencies, are arranged in the terminal housing. The directional coupler or the circulator and, where applicable, the single-pole, double-throw switch suitable for high frequencies, are thus located outside the metal housing, which is normally closed, of implantable devices of this type, and electromagnetic interference within the closed metal housing of the implantable device is effectively avoided. Building on the latter notion, it is advantageous, in the case of a terminal housing comprising at least one terminal for an electrode line and a filter feedthrough connected thereto, for the directional coupler or the circulator to be connected, between the terminal for the electrode line and the filter feedthrough, to the terminal for the electrode line, where applicable via the single-pole, double-throw switch suitable for high frequencies. This means that the terminal housing, as usual, comprises a filter feedthrough that serves to guide signals from the electrode line into the enclosed metal housing of the implantable device and vice versa. Stimulation pulses, for example, from the closed metal housing, are to be fed into the electrode line. Since the test apparatus is connected to the actual terminal for the electrode line between the filter feedthrough and said terminal, that is to say, for example, the single-pole, double-throw switch suitable for high frequencies is connected between the filter feedthrough and terminal, it is possible to produce the test apparatus entirely outside the closed metal housing.

In accordance with a further variant, a transceiver generally provided in the implantable device for data communication is to be used also as a test signal generator. This is based on the finding that transceivers of this type are typically able to generate high-frequency signals, which are also suitable as test signals for electrode fault detection. In addition, transceivers of this type can receive and process the reflected decoupled test signal. For this purpose, the transceiver provided for data communication and also serving as a test signal generator can be connected to the evaluation unit of the test apparatus. During operation for electrode fault detection, the transceiver thus generates the test signal, which is fed via the directional coupler or the circulator and, where applicable, the single-pole, double-throw switch suitable for high frequencies, into the electrode line and is reflected therein in part. The returning reflected test signal is decoupled again from the electrode line via the circulator or the directional coupler and is fed again to the transceiver (which then acts as a receiver). A reflected test signal, possibly demodulated by the transceiver, can then be analyzed by the evaluation unit and/or compared with reference signals.

In accordance with a further variant of the present invention, at least the directional coupler or also the circulator is integrated into the implantable electrode line itself in order to couple an electrical test signal into at least one electrical conductor of the electrode line and also to decouple the reflected test signal from the electrical conductor of the electrode line. The entire test apparatus may be integrated into the electrode line, where appropriate. In any case, it is possible to integrate the directional coupler or the circulator, but in particular the directional coupler, into the electrode line.

Should the electrode line be an electrode line for connection to an implantable device, which accordingly comprises a conventional electrode plug, it is advantageous if a test apparatus of the type described and claimed here is integrated into the electrode plug.

A method for testing an electrical conductor of an implantable electrode line is also proposed in accordance of the present invention and comprises the following method steps:
 coupling a test signal into the electrical conductor;
 decoupling the test signal reflected in the electrical conductor from the electrical conductor; and
 evaluating the reflected test signal.

Further features, aspects, objects, advantages, and possible applications of the present invention will become apparent from a study of the exemplary embodiments and examples described below, in combination with the Figures, and the appended claims.

DESCRIPTION OF THE DRAWINGS

The present invention will now be explained in greater detail of the basis of exemplary embodiments with reference to the Figures, in which.

DETAILED DESCRIPTION

Figure 1:
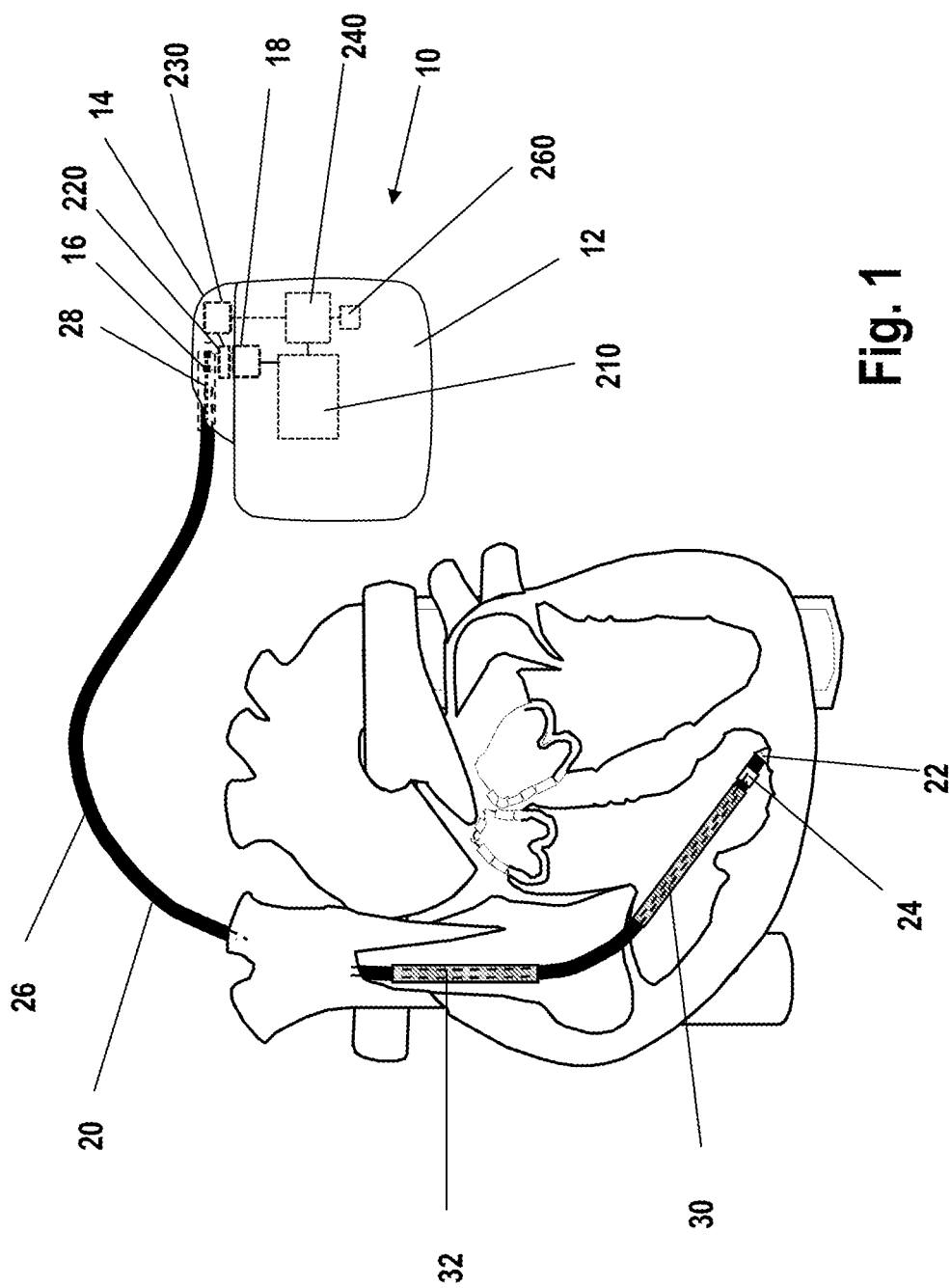
FIG. 1 shows, as implantable medical devices, an implantable heart stimulator 10 and an implantable electrode line 20 connected thereto.

The implantable heart stimulator 10 may be a cardiac pacemaker or a cardioverter/defibrillator (ICD). In the illustrated exemplary embodiment, the heart stimulator 10 is a ventricular cardiac pacemaker and defibrillator. Other known heart stimulators are dual-chamber cardiac pacemakers for stimulation of the right atrium and of the right ventricle, or biventricular cardiac pacemakers, which can also stimulate the left ventricle in addition to the right ventricle.

Stimulators of this type typically have a housing 12, which generally consists of metal and is thus electrically conductive and can serve as a large-area electrode pole. A terminal housing 14 is typically fastened to the outer face of the housing 12 and is also referred to as a header. A header of this type typically comprises a terminal 16 with contact sockets for receiving plug contacts of an electrode line. The contact sockets have electrical contacts, which are connected via corresponding lines and usually a filter feedthrough 18 to an electronics unit 210 arranged in the housing 12 of the heart stimulator 10.

Electrode poles in the form of a point or tip electrode 22 and a ring electrode 24 arranged in the vicinity thereof are arranged in a manner known per se at the distal end of the electrode line 20. The electrode poles 22 and 24 are designed such that they are used, depending on the function of a heart stimulator to which the electrode line 20 is connected, to sense electrical potentials of the heart tissue (myocardium), or are designed to deliver electrical signals, for example, to deliver stimulation pulses to the surrounding heart tissue. FIG. 1 shows how the electrode poles, that is to say the tip electrode 22 and the ring electrode 24, in the event of application of the electrode line 20, are located in the apex of the right ventricle of a heart.

Both the tip electrode and the ring electrode 24 are electrically connected in each case via at least one electrical conductor 26 to an electrode line plug 28 at the proximal end of the electrode line 20. The electrode line plug 28 has electrical contacts which correspond to the electrical contacts of the contact socket of the terminal 16 in the terminal housing 14 of the implantable heart stimulator. The electrical conductors 26 in the electrode line 20 can be formed, for example, as approximately elongate cable conductors or as helically coiled conductors. Such conductors, which electrically conductively connect the functional electrode poles to electrical contacts of the plug contact at the proximal end of the electrode line 20, will also be referred to within the scope of this text as functional conductors, since, for example, they transmit electrical signals used for therapy from the plug contact to the respective electrode pole or guide sensed signals representing electrical potentials from the respective electrode pole to the plug contact and are therefore used for the basic function of the medical device.

The electrical conductors 26, which connect the electrode poles 22 and 24 to the electrical contacts of the plug 28 of the electrode line 20, are surrounded over the majority of their length by an insulating sleeve, such that electrical contact of the tissue of the heart is produced selectively via the electrode poles.

Besides the electrode poles 22 and 24, which are typically used for stimulation of the heart tissue (in this case ventricular stimulation), the electrode line 20 also has two electrode poles 30 and 32, which have a greater area and are used as defibrillation electrodes and are formed by at least one bare helically coiled wire.

Those component parts of the implantable device 10 that constitute a test apparatus for electrode fault detection are additionally illustrated in FIG. 1. These component parts include a single-pole, double-throw switch 220 suitable for high frequencies, which is connected between the terminal 16 and the filter feedthrough 18 and by means of which the functional conductors of the electrode line 20 can be electrically connected either to the filter feedthrough 18 or alternatively to a directional coupler 230. A circulator may also be provided instead of the directional coupler 230.

The directional coupler 230 is designed such that a test signal containing high-frequency signal components can couple into one or more of the conductors 26 of the electrode line 20 via the double-throw switch 220, and signal components of the test signal reflected in the electrode line 20 can be decoupled again. The test signal to be coupled into the conductor or conductors 26 is generated and output by a test signal generator 240. In the illustrated exemplary embodiment, the test signal generator 240 is simultaneously a transceiver for a wireless data communication with the implantable device 10.

Returning (reflected) signal components of the test signal are fed via the double-throw switch 220 into the directional coupler 230 and, in turn, to the transceiver 240, which is in turn connected to an evaluation unit 260. This is designed to compare a reflected test signal (more specifically the reflected returning signal components of the test signal) with a corresponding reference signal.

For testing of the electrode line 20 for the purpose of electrode fault detection, the transceiver 240 is thus connected as a test signal generator and evaluation unit via the directional coupler 230 and the accordingly switched double-throw switch 220 to at least one conductor 26 of the electrode line 20.

With normal operation of the implantable device 10, the double-throw switch 220 is switched such that the conductor or conductors 26 of the electrode line 20 is/are connected to the filter feedthrough 18 and, via this, to the rest of the electronics unit 210 (for example, for a therapy control unit). Since the directional coupler 230 in this case is no longer connected to the conductor (s) 26 of the electrode line 20, the test apparatus also cannot compromise the regular operation of the implantable device 10.

It is only of secondary importance that the transceiver 240 is also connected to the rest of the electronics unit 210 (therapy control unit) in order to allow a data communication, for example, with an external device, in the conventional manner known per se.

Figure 2:
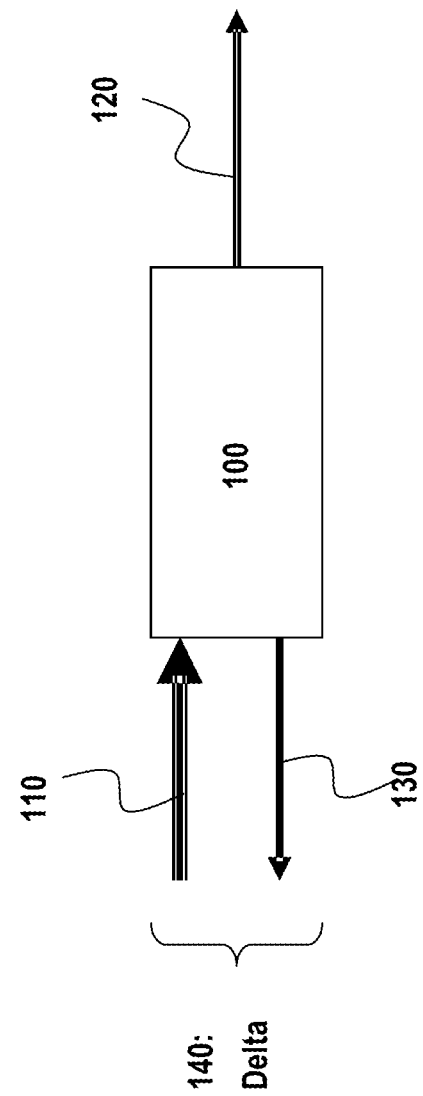
FIG. 2 shows a sketch for explaining the principle forming the basis of the present invention.

The basic principle of the measurement to be carried out by the test apparatus is illustrated in FIG. 2. The measurement is based on the reflections on lines, such as the conductors 26 of the electrode line 20, said reflections occurring at each discontinuity on the electrode line 100. For the measurement, the electrode line 100 is first exposed to a test signal 110 of known frequency, amplitude and phase, and a wave is thus generated along at least one conductor 26 of the electrode line 100. Part 120 of this wave is delivered from the electrode line into the surrounding environment and a further part 130 is reflected in the electrode line at discontinuities thereof. This part 130 represents the returning reflected test signal 130 and can be separated from the coupled-in wave with the aid of the directional coupler 230 (see e.g., FIGS. 1 and 3). The difference 140 between the coupled-in test signal 110 and the reflected decoupled test signal 130 can thus be ascertained and evaluated as an indicator for an electrode fault.

For the measurement for electrode fault detection, a test signal 110 is preferably generated that has the form of a rectangular pulse train and is coupled into the electrode line to be examined in order to enable a distinction between the test signal 110 and other signals, for example, cardiac events and interference signals.

Figure 3:
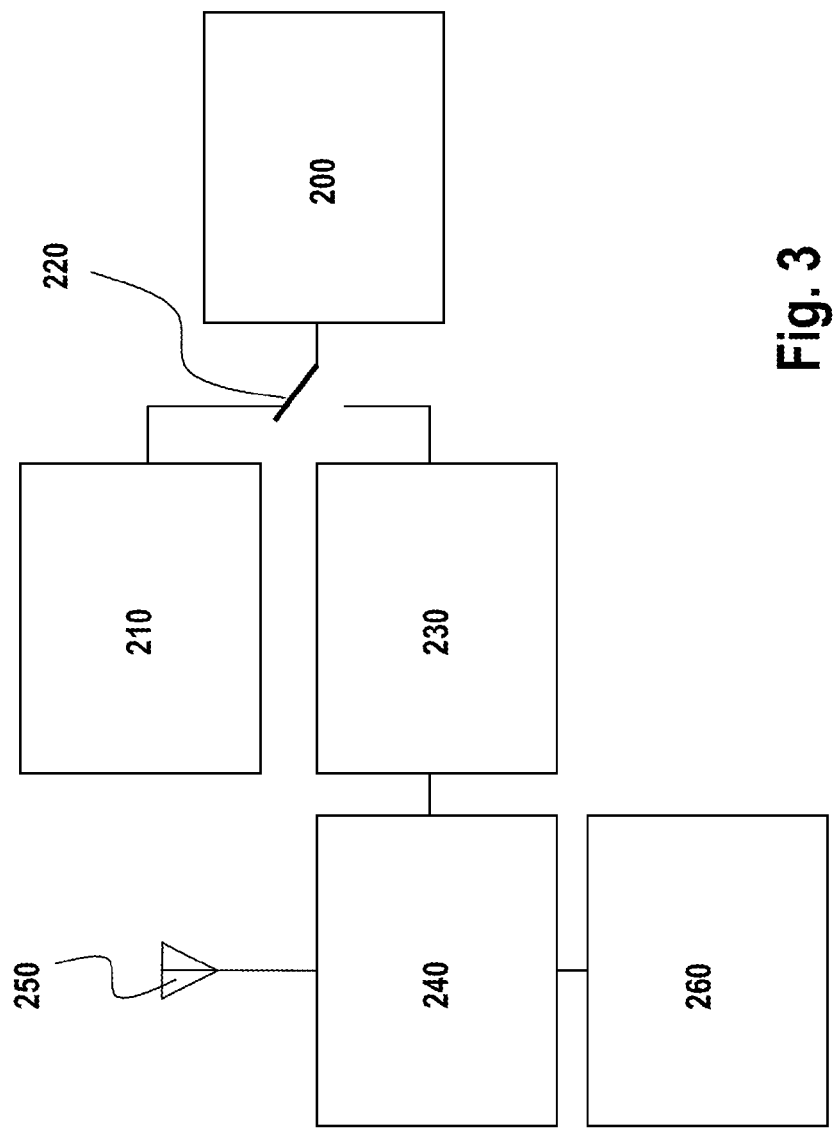
FIG. 3 shows an example for a test apparatus according to the present invention.

A possible block diagram for the proposed test apparatus for electrode fault detection is illustrated in FIG. 3. The electrode line 200 is always connected during normal operation to the therapy control unit 210 of the implantable device via a double-throw switch 220 suitable for high frequencies.

For a test of the electrode line by means of a reflection measurement, this electrode line 200 is then connected by means of the double-throw switch 220 to a directional coupler 230. This is in turn connected to the RF transceiver 240, which is provided in the implantable device and which is normally used for communication between the implantable device and external devices by means of an antenna 250. For the reflection measurement, the RF transceiver 240 is connected to an additional output in order to couple the test signal into the directional coupler 230 and is provided with an additional input in order to receive the reflected wave (the reflected test signal). The RF transceiver 240 is further equipped with an evaluation unit 260, which is used to establish the difference between the irradiated and received wave. In this case, the evaluation unit 260 is connected indirectly to the directional coupler 230. The evaluation unit 260 may also be connected directly to the directional coupler in such a way that said evaluation unit evaluates the returning wave (the reflected test signal) in order to analyze the reflection behavior on the electrode line.

The directional coupler 230 is preferably a microstrip directional coupler in the terminal housing 14 of the implantable device 10, switchable to the individual conductors 26, which are to be examined, of the electrode line 20 by means of the single-pole, double-throw switch 220 suitable for high frequencies which, for example, can be formed either by a MEMS relay (advantageous in the case of EMI) or transistors (disadvantageous in the case of EMI). With this arrangement, the EMI filter can also be used in the feedthroughs 18.

For testing of the electrode line for electrode line faults, the test apparatus is connected by means of the double-throw switch to the electrode line in such a way that the rest of the circuit of the implantable device is decoupled from this test apparatus, that is to say the EMI capacitors and all further capacitive and inductive components of the electronics unit 210 of the implantable device do not influence the reflection measurement.

A testing of this type of the electrode line is preferably carried out at recurring intervals, that is to say cyclically.

The returning wave (that is to say the reflected test signal) is preferably evaluated on the basis of a comparison with a previously established reference signal, which was recorded with a demonstrably intact electrode system (for example, comparison with reference from the implantation or with trend values).

The information of the electrode fault evaluation is preferably stored in the implantable device and is read out and displayed during the aftercare process by an external device, for example, a programming device. Alternatively or additionally, the information concerning the electrode fault evaluation may be transmitted to the doctor via a remote monitoring system. It is alternatively or additionally possible to automatically adapt the operating mode or other operating parameters of the implant and/or to deliver a signal to the patient (e.g., sound/vibration or the like) and/or to trigger an automatic reconfiguration of the used electrode lines, for example, a switchover from bipolar to unipolar or vice versa, depending on the information of the electrode fault evaluation. The variants specified here provide corresponding advantageous embodiments of the implantable device.

The analysis of the reflected test signal may optionally also be used to diagnose electrode dislocation because the reflection properties of the electrode line are also dependent on the electrical properties of the immediate vicinity of a respective electrode pole at the distal end of a respective electrical conductor of the electrode line. Accordingly, an implantable device is preferred which is designed to evaluate a reflected test signal in terms of such signal features which provide information concerning the surrounding environment of a respective electrode pole, for example, in terms of the wall contact thereof.

In respect of the arrangement of the test apparatus or of parts of the test apparatus, the following variants are advantageous:

At least parts of the test apparatus are housed in the housing 12 of the implantable device 10.

The test apparatus is housed in the terminal housing 14 of the implantable device 10, such that filtered feedthroughs can still be used.

The test apparatus is housed within the electrode line plug 28 or within the electrode line 12.

The directional coupler is an integral part of the electrode line 20 or of the electrode line plug 28.

The bandwidth of the directional coupler is preferably selected such that the transceiver generally already provided for the RF communication can be used for the signal generation and the analysis of the returning wave. Here, preferred frequencies are the MICS band, the ISM band (especially also the BlueTooth LE band) or a GSM/UMTS band.

The bandwidth of the directional coupler 230 can additionally or alternatively also be set to the expected electrode conductor lengths ($\lambda$; $\lambda/2$; $\lambda/4$) and, for example, is in a range of 400-800 MHz corresponding to a wavelength $\lambda$ between approximately 40 cm to 70 cm.

It should be mentioned that the present invention is explained within the scope of this exemplary embodiment on the basis of a right-ventricular cardiac pacemaker and defibrillator. Within the context of the present invention, an ablation electrode line, for example, may also serve in principle as a medical device; however, said line, in the event of the application, likewise protruding into the heart of a patient and being controlled by a device arranged outside the patient and connected thereto for this purpose. Further electronic implants connected to electrode or sensor lines, for example, neurostimulators or pressure sensor implants, can also be considered for the application of the present invention.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

LIST OF REFERENCE NUMERALS 10 heart stimulator
12 housing
14 terminal housing
16 terminal (contact sockets) for electrode line
18 filter feedthrough
20 electrode line
22 point or tip electrode
24 ring electrode
26 electrical conductor
28 electrode line plug
30, 32 electrode poles
100 electrical conductor
110 coupled-in test signal
120 part of the wave exiting into the surrounding environment
130 reflected test signal
200 electrode line
210 electronics unit (therapy control unit)
220 double-throw switch
230 directional coupler
240 test signal generator (transceiver)
250 antenna
260 evaluation unit

We claim:

1. An implantable medical device including a test apparatus for an implantable electrode line comprising at least one electrical conductor, the test apparatus comprising:
a test signal generator for generating an electrical test signal;
a directional coupler or a circulator connected with the test signal generator for coupling the electrical test signal into the at least one electrical conductor of the electrode line and for decoupling a reflected test signal from the electrical conductor of the electrode line; and,
an evaluation unit connected at least indirectly to the directional coupler or the circulator to detect a fault of the electrode line, wherein the fault comprises an inhomogeneity of the electrode conductor, wherein the evaluation unit compares the reflected signal to a reference signal,
wherein the directional coupler or the circulator is connected to the electrical conductor of the electrode line via a single-pole, double-throw switch suitable for high frequencies, such that the directional coupler or the circulator, the test signal generator and the evaluation unit are disconnected from the electrical conductor during normal operation of a device connected to the electrical conductor.

2. The implantable medical device as claimed in claim 1, wherein the at least one electrical conductor is formed as helically coiled conductors.

3. The implantable medical device as claimed in claim 1, wherein the reference signal is previously established and recorded with an intact electrode system.

4. The implantable medical device as claimed in claim 1, wherein the test signal contains high-frequency signal components and is a steep voltage pulse.

5. The implantable medical device as claimed in claim 1, wherein the directional coupler is formed on the basis of microstrip technology.

6. The implantable medical device as claimed in claim 1, wherein the directional coupler has a bandwidth which comprises at least part of the frequency range between 400 MHz and 2.4 GHz.

7. The implantable medical device as claimed in claim 1, wherein the directional coupler has a bandwidth which comprises at least part of the frequency range between 400 MHz and 800 MHz.

8. The implantable medical device as claimed in claim 1, wherein the directional coupler or the circulator is connected to the electrode line or to a terminal for an electrode line via the single-pole, double-throw switch suitable for high frequencies.

9. The implantable medical device as claimed in claim 8, wherein the implantable device further comprises a terminal housing, and at least the directional coupler or the circulator and the single-pole, double-throw switch suitable for high frequencies are arranged in the terminal housing.

10. The implantable medical device as claimed in claim 9, wherein the terminal housing comprises at least one terminal for an electrode line and a filter feedthrough connected thereto, and the directional coupler or the circulator is connected, between the terminal for an electrode line and the filter feedthrough, to the terminal for an electrode line via the single-pole, double-throw switch suitable for high frequencies.

11. The implantable medical device as claimed in claim 1, wherein the test signal generator is a transceiver for data communication of the implantable device.

12. An implantable electrode line for connection to an implantable device, comprising:
an electrode line plug at a proximal end of an electrode line, wherein the electrode line plug contains a test apparatus as claimed in claim 1.

13. The implantable medical device as claimed in claim 1, further comprising at least one electrode connected to the electrical conductor of the electrode line, wherein the fault detected by the evaluation unit based on a comparison of the reflected signal with the reference signal further comprises electrode dislocation.

14. The implantable medical device as claimed in claim 1, wherein the implantable medical device comprises an implantable cardiac pacemaker or defibrillator.

15. An implantable electrode line as part of an implantable device or for connection to an implantable device, comprising:
a directional coupler which is designed to couple an electrical test signal into at least one electrical conductor of the electrode line and also to decouple the reflected test signal from the electrical conductor of the electrode line,
wherein the directional coupler is connected to the electrical conductor of the electrode line via a single-pole, double-throw switch suitable for high frequencies, such that the directional coupler, the test signal generator and the evaluation unit are disconnected from the electrical conductor during normal operation of a device connected to the electrical conductor.

* * * * *